(12) United States Patent
Yakovlev et al.

(10) Patent No.: US 10,818,890 B2
(45) Date of Patent: Oct. 27, 2020

(54) POWER SOURCE FOR AN IMPLANTABLE MEDICAL DEVICE

(71) Applicant: Medtronic, Inc., Minneapolis, MN (US)

(72) Inventors: Vadim A. Yakovlev, Fridley, MN (US); Kenneth Michie, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 779 days.

(21) Appl. No.: 14/317,092

(22) Filed: Jun. 27, 2014

(65) Prior Publication Data
US 2015/0297898 A1    Oct. 22, 2015

Related U.S. Application Data

(60) Provisional application No. 61/982,402, filed on Apr. 22, 2014, provisional application No. 61/982,426, filed on Apr. 22, 2014.

(51) Int. Cl.
*H01M 2/06*    (2006.01)
*A61N 1/378*    (2006.01)
(Continued)

(52) U.S. Cl.
CPC .............. *H01M 2/06* (2013.01); *A61N 1/378* (2013.01); *B23K 9/0026* (2013.01);
(Continued)

(58) Field of Classification Search
None
See application file for complete search history.

(56) References Cited

U.S. PATENT DOCUMENTS

| 4,140,891 A | 2/1979 | Lenox |
| 5,250,373 A | 10/1993 | Muffoletto et al. |

(Continued)

FOREIGN PATENT DOCUMENTS

| EP | 0051135 A1 | 10/1981 |
| EP | 0597214 A1 | 12/1995 |

(Continued)

OTHER PUBLICATIONS

(PCT/US2015/026586) PCT Notification of Transmittal of the International Search Report and the Written Opinion of the International Searching Authority, dated Jul. 29, 2015, 9 pages.
(Continued)

*Primary Examiner* — Daniel S Gatewood
(74) *Attorney, Agent, or Firm* — Mueting Raasch Group (57) ABSTRACT

A battery having an electrode assembly located in a housing that efficiently utilizes the space available in many implantable medical devices is disclosed. The battery housing includes a cover and a case. The electrode assembly includes an anode tab and a cathode tab that are coupled to the cover and to a feedthrough pin disposed on the cover. The coupling of the anode tab to the cover defines an anode terminal while the coupling of the cathode tab to the feedthrough pin defines the cathode terminal. The anode and cathode tabs are aligned with the feedthrough pin and the connection point at the cover such that the tabs and feedthrough pin overlap each other along a common plane that is perpendicular to a plane that is defined by a major surface of the cover.

9 Claims, 8 Drawing Sheets

(51) Int. Cl.
  *H01M 2/20* (2006.01)
  *H01M 2/30* (2006.01)
  *B23K 9/00* (2006.01)
  *A61N 1/362* (2006.01)
  *H01R 43/02* (2006.01)

(52) U.S. Cl.
  CPC .............. *H01M 2/204* (2013.01); *H01M 2/30* (2013.01); *A61N 1/3622* (2013.01); *H01M 2220/30* (2013.01); *H01R 43/0214* (2013.01)

(56) References Cited

U.S. PATENT DOCUMENTS

| | | | |
|---|---|---|---|
| 5,312,458 A | 5/1994 | Muffoletto et al. | |
| 5,458,997 A | 10/1995 | Crespi et al. | |
| 5,486,215 A * | 1/1996 | Kelm | H01M 2/0404 |
| | | | 29/623.1 |
| 5,716,729 A | 2/1998 | Sunderland et al. | |
| 6,011,235 A | 1/2000 | Mukai et al. | |
| 6,855,456 B2 | 2/2005 | Taylor et al. | |
| 7,056,618 B2 | 6/2006 | Hirano et al. | |
| 7,368,680 B2 | 5/2008 | Sakurai et al. | |
| 7,479,349 B2 | 1/2009 | O'Phelan et al. | |
| 7,544,220 B2 * | 6/2009 | Zhao | H01M 2/0473 |
| | | | 29/623.4 |
| 2004/0127952 A1 | 7/2004 | O'Phelan et al. | |
| 2006/0166088 A1 * | 7/2006 | Hokanson | A61N 1/378 |
| | | | 429/161 |
| 2009/0100665 A1 | 4/2009 | Berger et al. | |
| 2011/0123856 A1 | 5/2011 | Dai | |
| 2013/0059197 A1 * | 3/2013 | Huang | H01M 2/26 |
| | | | 429/178 |

FOREIGN PATENT DOCUMENTS

| | | |
|---|---|---|
| EP | 1510278 A1 | 3/2005 |
| FR | 2783734 A1 | 3/2000 |
| GB | 900271 | 7/1962 |
| WO | 02/02186 A2 | 1/2002 |
| WO | 2010/066414 A1 | 6/2010 |
| WO | 2010/111159 A2 | 9/2010 |

OTHER PUBLICATIONS

EspaceNet Machine Translation of WO 2010/066414 A1 to Karakas (translated Dec. 2016).

* cited by examiner

POWER SOURCE FOR AN IMPLANTABLE MEDICAL DEVICE

CROSS-REFERENCE TO RELATED APPLICATIONS

This application claims the benefit of priority from U.S. Provisional Application Nos. 61/982,402 and 61/982,426, both filed on Apr. 22, 2014, the contents of which are incorporated herein by reference in their entirety.

FIELD

The disclosure relates to implantable medical devices and, more particularly to power sources, such as batteries, that are used to power implantable medical devices.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Some of those maladies can be corrected or treated with implantable medical devices (IMDs), such as implantable pacemakers, implantable cardioverter defibrillator devices, cardiac resynchronization therapy defibrillator devices, or combinations thereof. The electrical therapy produced by an IMD may include, for example, pacing pulses, cardioverting pulses, and/or defibrillator pulses to reverse arrhythmias (e.g. tachycardias and bradycardias) or to stimulate the contraction of cardiac tissue (e.g. cardiac pacing) to return the heart to its normal sinus rhythm.

The IMDs are preferably designed with shapes that are easily accepted by the patient's body while minimizing patient discomfort. As a result, the corners and edges of the devices are typically designed with generous radii to present a package having smoothly contoured surfaces. It is also desirable to minimize the volume and mass of the devices to further limit patient discomfort. As such, efforts towards miniaturization of the IMD package also require a reduction in the sizes and form factors of the components housed within the package.

In general, the IMDs include a power source (battery) and electronic circuitry, such as a pulse generator and/or a processor module, which are hermetically sealed within a housing (can). The electrical energy for the electrical therapy delivered by IMDs is generated by delivering electrical current from the battery. The battery is a volumetrically constrained system. The sizes or volumes of components that are contained within a battery (cathode, anode, separator, current collectors, electrolyte, etc.) cannot in total exceed the available volume of the battery case. The arrangement of the components affects the amount or density of active electrode material, which can be contained within the battery case.

Typically, a battery includes corrosive material (e.g., the electrolyte). Any leakage of the corrosive material may undesirably damage the battery and/or the electrical components of the device (e.g., the implantable medical device) that the battery is used with. Such damage may generally cause the device to function improperly or otherwise cause it to cease operating altogether. In addition, if used in a medical device surgically implanted within a patient's body, as described above, accessibility to the device may be difficult for repair or replacement.

One approach to isolating the corrosive material involves using an electrical feedthrough arrangement for the battery to function as an intermediary. The feedthrough arrangement is designed to provide electrical connection between the battery and the other electrical components of the implantable medical device, and to maintain environmental isolation between the corrosive material within the battery and the other electrical components within the device. This isolation is, in part, achieved by using feedthrough pins that are generally corrosion resistant. However, effectively coupling these pins to the one or more of the electrodes in contact with the corrosive material within the battery can be difficult.

Therefore, there remains a need for improvements to methods of constructing power sources.

SUMMARY

In general, the disclosure is directed to articles of an implantable medical device that include a weld that bonds a first component and a second component of the article. In accordance with some embodiments, the articles of the implantable medical device include a battery. The battery for an implantable medical device comprises an electrode assembly enclosed in a battery case. The battery includes a cathode tab and an anode tab that are coupled to the electrode assembly.

In one aspect, the disclosure describes coupling techniques that facilitate miniaturization of the battery. The techniques enable construction of a battery with a tight form factor that enables a reduction in the overall volume of the battery.

In another aspect, the battery is configured having the anode tab and the cathode tab being positioned in an overlapping orientation such that the tabs are generally parallel along a common plane in relation to a major planar surface of the cover. A feedthrough pin is disposed on the cover for providing a terminal for connection of the battery to circuitry of the implantable medical device. The anode tab is electrically coupled to the cover and the cathode tab is electrically coupled to the feedthrough pin.

In another aspect, methods for fabrication of batteries for implantable medical devices include the tasks of: providing an electrode assembly that includes a first tab and a second tab, providing a battery cover having a feedthrough assembly that includes a feedthrough pin, aligning the electrode assembly with the battery cover such that the feedthrough pin intersects the first tab at a first connection point and the second tab intersects the battery cover at a second connection point such that the second connection point is oriented to overlap with the first connection point, and connecting the electrode assembly to the battery cover to form a joint unit whereby the feedthrough pin is electrically coupled to the first tab at the first connection point and the second tab is electrically coupled to the cover at the second connection point.

In another aspect, a resistance spot welding manufacture includes a first set of components and a set of components, wherein each set of components is oriented to overlap in a common lateral axis. The resistance spot welding manufacturing includes a first weld joint bonding the first set of components and a second weld joint bonding the second set of components. In some embodiments, at least one of the components in the first set of components and at least one of the components in the second set of components is formed from a dissimilar material.

In an additional aspect, a method of forming a resistance spot weld includes aligning a first set of components and a second set of components such that at least a portion of the components overlap along a common lateral axis. The method includes delivering a current through the first set of components and the second set of components to simultaneously form a first weld joint and a second weld joint between the first set of components and the second set of components, respectively. In some embodiments, the current delivered through the first set of components may be different from the current delivered through the second set of components.

The details of one or more aspects of the disclosure are set forth in the accompanying drawings and the description below. Other features, objects, and advantages will be apparent from the description and drawings, and from the claims.

BRIEF DESCRIPTION OF THE DRAWINGS

Various exemplary embodiments of the compositions and methods according to the invention will be described in detail, with reference to the following figures wherein.

The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

DETAILED DESCRIPTION

In general, the disclosure is directed to articles of an implantable medical device that include a weld that bonds a first component and a second component of the article. For example, an article of the implantable medical device includes a battery.

The disclosure is not limited to any one type of application for the coupling techniques. For example, while embodiments are described and shown herein illustrating batteries in implantable medical devices with respect to medical applications, the disclosure should not be limited as such.

As used herein, the terms battery or batteries include a single electrochemical cell or cells. Batteries are volumetrically constrained systems in which the components of the battery cannot exceed the available volume of the battery case. Furthermore, the relative amounts of some of the components can be important to provide the desired amount of energy at the desired discharge rates. A discussion of the various considerations in designing the electrodes and the desired volume of electrolyte needed to accompany them in, for example, a lithium/silver vanadium oxide (Li/SVO) battery, is discussed in U.S. Pat. No. 5,458,997 (Crespi et al.). Generally, however, the battery must include the electrodes and additional volume for the electrolyte required to provide a functioning battery. In certain embodiments, the battery is hermetically sealed.

In certain embodiments, the batteries are directed to high current batteries that are capable of charging capacitors with the desired amount of energy in the desired amount of time. In certain embodiments, the desired amount of energy is typically at least about 20 joules. Further embodiments involve the energy amount being about 20 joules to about 40 joules. In certain embodiments, the desired amount of time is no more than about 20 seconds. Further embodiments involve the desired amount of time being no more than about 10 seconds. These energy and time values can typically be attained during the useful life of the battery as well as when the battery is new. As a result, in certain embodiments, the batteries typically deliver up to about 5 amps at about 1.5 to about 2.5 volts, in contrast to low rate batteries that are typically discharged at much lower currents. Furthermore, the batteries are able to provide these amounts of energy repeatedly. In certain embodiments, the battery can provide these amounts of energy with a time delay of no more than about 30 seconds. Further embodiments involve the time delay being no more than about 10 seconds.

Figure 1:
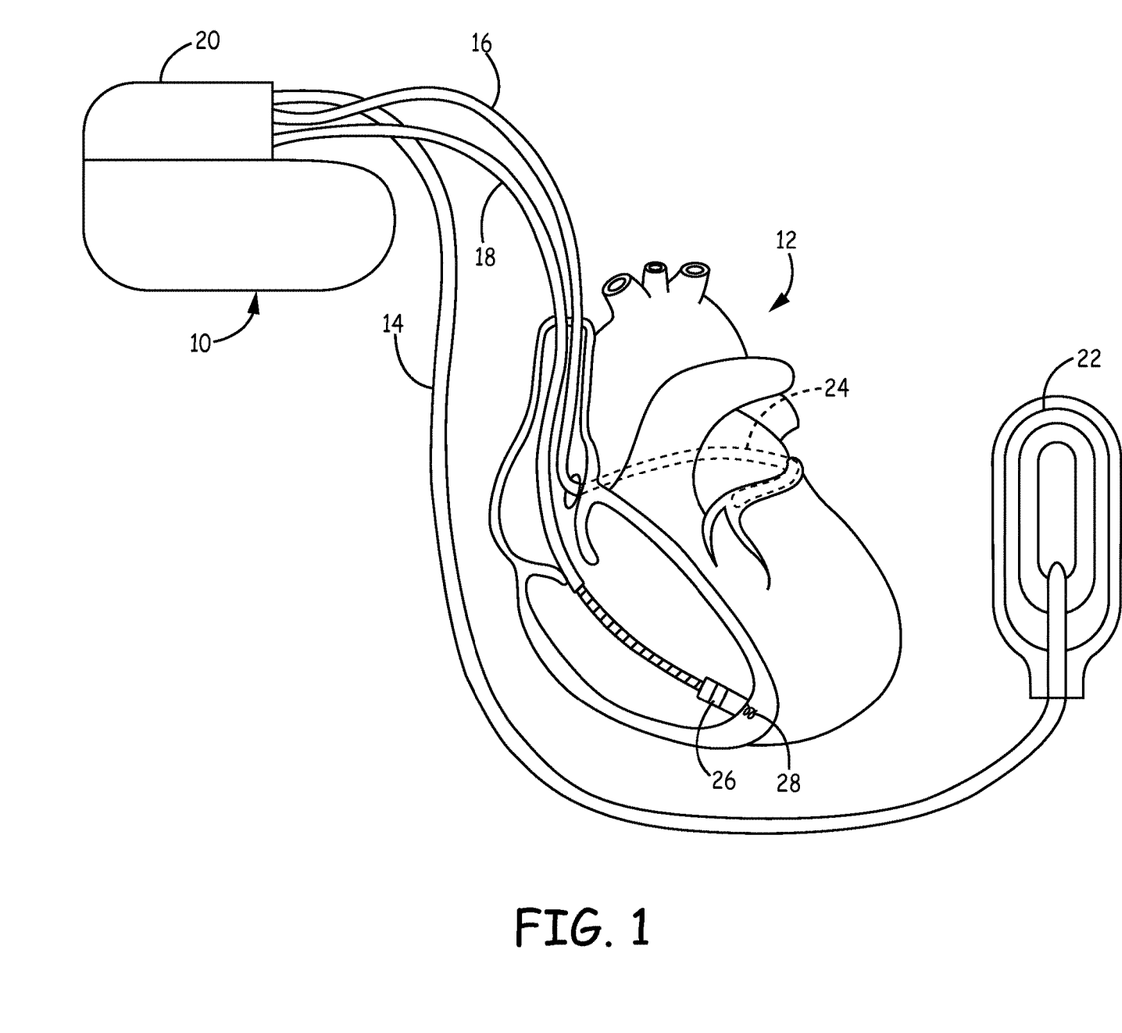
FIG. 1 is a simplified schematic view of an implantable medical device ("IMD") incorporating an electrochemical cell in accordance with certain embodiments of the invention.

FIG. 1 is a simplified schematic view of an implantable medical device ("IMD") 10. The IMD 10 is shown with a relationship to a human heart 12. However, the IMD 10 shown may assume a wide variety of forms. For example, the IMD 10 may be an implantable neurostimulator, or an implantable drug pump, a cardiomyostimulator; a biosensor, and the like.

The IMD 10 includes associated electrical leads 14, 16 and 18, although it should be appreciated that the IMD 10 can include any number of leads suitable for a particular application. The leads 14, 16 and 18 are coupled to the IMD 10 by means of a multi-port connector block 20, which contains separate ports for each of the leads 14, 16, and 18. The leads 14, 16, and 18 may be implanted in any known implantation location including, inside the heart 12, or externally such as in contact with the heart 12 tissue or over the ribcage. In the illustration, electrical therapy is delivered between any one of the electrodes 22, 24, 26, and 28. The electrodes 22-28 are also employed to sense electrical signals indicative of cardiac contractions.

As previously described, the IMD 10 can assume a wide variety of forms as are known in the art. Generally, IMDs include one or more of the following elements: (a) a device housing (e.g., a case), (b) one or more capacitors disposed within the device housing, (c) a battery disposed within the device housing and operatively connected to the capacitor, and (d) circuitry disposed within the device housing providing electrical connection between the battery and the capacitor.

Figure 2:
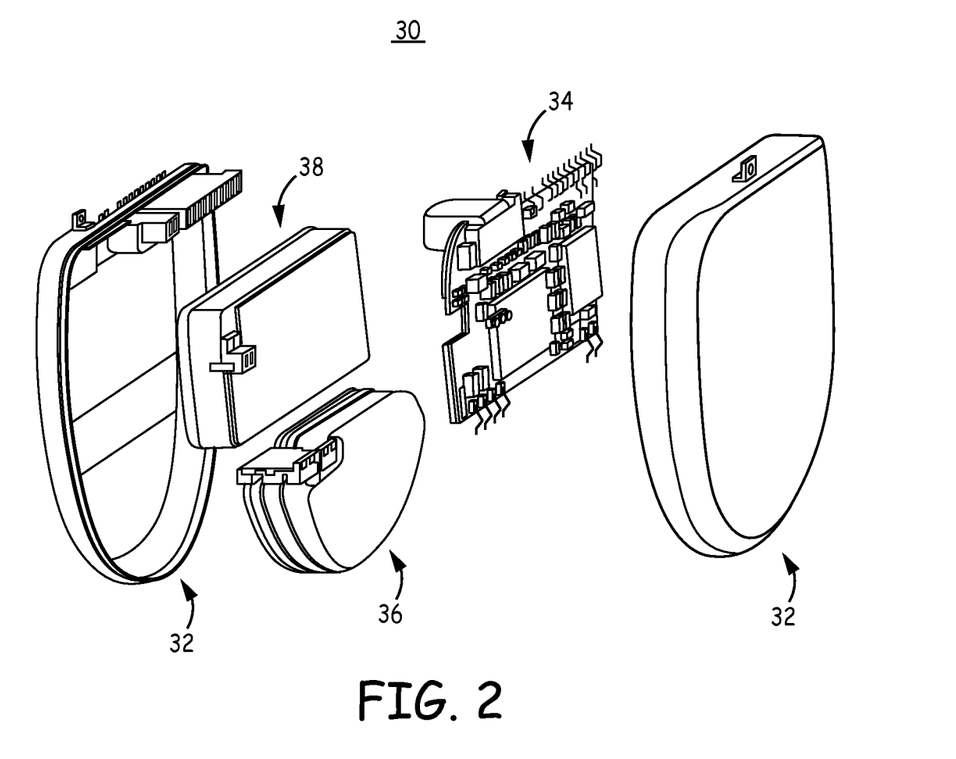
FIG. 2 is an exploded perspective view of an IMD without cover in accordance with certain embodiments of the invention.

FIG. 2 depicts exemplary illustrations and general locations of elements of an IMD 30. As shown, the IMD 30 includes a device housing or case 32 (having two halves), an electronics module 34 (the circuitry), capacitor(s) 36, and an electrochemical cell 38 (the battery). Each of these components of the IMD 30 is preferably configured for one or more particular end-use applications. For example, the electronics module 34 is configured to perform one or more sensing and/or stimulation processes. The electrochemical cell 38 provides the electrical energy to charge and re-charge the capacitor(s) 36, and to also power the electronics module 34. According to certain embodiments, the electrochemical cell 38 may take the form of a rechargeable (secondary) lithium-ion battery, which may incorporate a negative active material comprised of Carbon, a positive active material of a lithium transition metal oxide, such as $LiCoO_2$, for example, and a lithium containing salt, such as $LiPF_6$ and an appropriate organic solvent for the $LiPF_6$ salt, for example. In other certain embodiments, the electrochemical cell 38 may be provided as a non-rechargeable (primary) lithium battery. It should be appreciated that the electrochemical cell 38 may take the form of various other battery types or electrochemical cells, either active or passive (battery packs), and, thus need not necessarily be limited to the aforementioned examples.

Electrochemical cells generally include one or more of the following components: (a) an electrode assembly including one or more of an anode and a cathode, (b) an electrolyte, and (c) a housing within which the electrode assembly and the electrolyte are disposed. In certain embodiments, the housing includes one or more of the following elements: (a) a cover, (b) a case with an open top to receive the cover, (c) at least one feedthrough assembly providing electrical communication from a first electrode of the electrode assembly and the implantable medical device circuitry (e.g., the electronics module 34), (d) a coupling providing electrical connection between the at least one feedthrough assembly and a first electrode of the electrode assembly, and (e) a coupling providing electrical connection between the case (or another feedthrough assembly) and a second electrode of the electrode assembly. The housing may optionally include one or more insulators including (a) a case liner adjacent to the case providing a barrier between the electrode assembly and the case, and (b) a head space insulator adjacent to the electrode assembly (e.g., proximate to the insulator adjacent to the cover) providing a barrier between the electrode assembly and the case.

Figure 3:
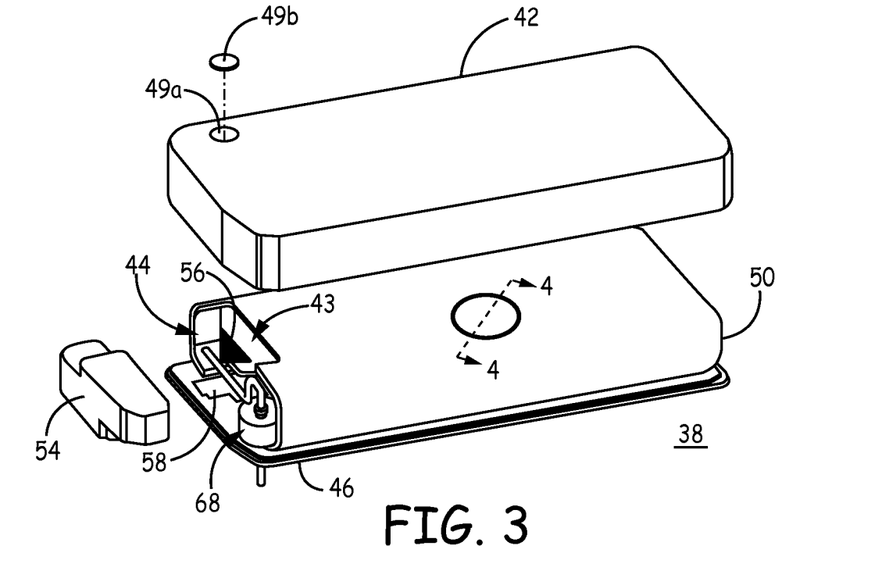
FIG. 3 illustrates a perspective view of an assembly of a battery in accordance with an exemplary embodiment of the present disclosure.
Figure 4:
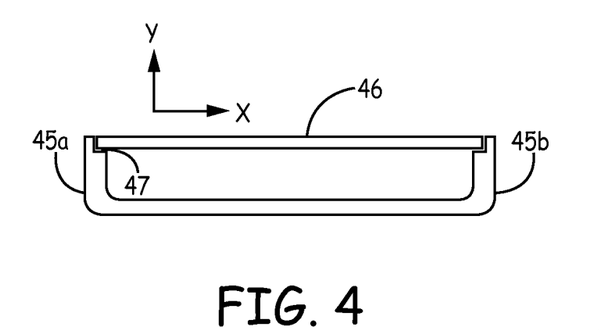
FIG. 4 illustrates a side cross-sectional view of an assembly of a battery in accordance with an exemplary embodiment of the present disclosure.

FIGS. 3 and 4 illustrate an assembly of a battery in accordance with an exemplary embodiment of the present disclosure. A battery 38 is illustrated having a shallow drawn battery case 42 and an electrode assembly 44. The battery case 42 is generally made of a medical grade titanium; however, it is contemplated that the case 42 could be made of almost any type of metal such as aluminum and stainless steel, as long as the metal is compatible with the battery's chemistry in order to prevent corrosion. The battery case 42 is designed to enclose the electrode assembly 44 and be sealed with a battery cover 46. A headspace 43 region may be included in the battery case 42 for housing insulators and the connector tabs (discussed below) that transfer electrical energy from electrode assembly 44 to the implantable medical device circuitry.

The battery case 42 is formed having a planar bottom portion, an open top to receive the cover 46, and at least two sides 45a, 45b extending from the bottom portion that may be radiused at intersections with the bottom portion. The planar bottom portion may define a plane along the (lateral) x-axis that is parallel to the plane defined by a major surface of the cover 46.

The battery cover 46 is held in place by a lip 47 that prevents the cover 46 from dropping within battery case 42. In an alternative embodiment, the lip may be located on the cover 46 to engage with the case 42. The cover 46 is welded to the case 42, such as through laser welding, although other methods of attachment are contemplated. For example, resistance welding, brazing, soldering and similar techniques may be employed and/or adhesive materials may be used to couple the cover 46 to the case 42.

The battery case 42 will also include a fillport 49a that is used to route the electrolyte into battery 38. The fillport preferably includes an opening that is formed on battery case 42 and is preferably hermetically sealed to ensure no electrolyte leakage. The fillport receives an electrolyte injection device that transfers electrolyte from the device to battery 38. Once the electrolyte has been injected within battery 38, a ball seal 49b may be placed within the opening to create a "press-fit" hermetic seal, which prevents any electrolyte from escaping through the opening. A secondary seal may subsequently be formed over the ball seal to provide a redundant seal. In yet another embodiment, a gasket seal or epoxy is utilized to plug the opening.

A case liner 50 may be provided to electrically isolate electrode assembly 44 from battery cover 46. The case liner 50 may be configured in the shape of the case 42 with dimensions that are slightly smaller so as to fit within the case 42. The walls of the case liner 42 define a hollow receptacle that receives the electrode assembly 44. Liner 50 may include an open end at the head space region 43 that leads into the hollow receptacle. As shown in FIG. 3, the case liner 50 is configured with slits at the open end to accommodate cathode tab 56 and anode tab 58. Case liner 50 is comprised of an electrically insulative material such as ETFE having a thickness of about 0.030 cm. (0.012 inches). However, it is contemplated that other thicknesses and materials could be used such as high density polyethylene (HDPE), polypropylene, polyurethane, fluoropolymers, and the like.

The battery 38 may also include a head space insulator 54 that is coupled at the open end of the case liner 50 so as to enclose the open end of the case liner 50. Although not shown in FIG. 3, head space insulator 54 may include components that are formed to be positioned between the anode tab 58 and the cathode tab 56. The components may be formed with a predetermined width such that a predetermined spacing is maintained between the cathode tab 56 and anode tab 58.

Case liner 50 performs several functions including working in conjunction with the head space insulator 54 to isolate battery case 42 and battery cover 46 from electrode assembly 44. Case liner 50 also provides mechanical stability for electrode assembly 44. In addition, case liner 50 serves to hold the coil assembly together which substantially aids in the manufacturing of battery 38. Since electrode assembly 44 is preferably a wound coil, case liner 50 also helps prevent assembly 44 from unwinding. Case liner 50 further provides protection for assembly 44 during handling and during the life of assembly 44. Finally, case liner 50 provides a thermal barrier between assembly 44 and cover 46 during the laser welding procedure that joins cover 46 with case 42.

Figure 5:
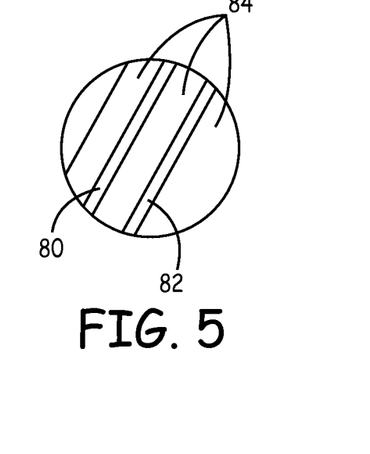
FIG. 5 illustrates a partial cutaway perspective view of the electrode assembly of the battery of FIG. 3.

FIG. 5 illustrates a partial cutaway perspective view of the electrode assembly 44 of the battery 38 of FIG. 3 along the lines 4-4. As illustrated, the electrode assembly 44 generally includes a first electrode 80, a second electrode 82, and a porous, electrically non-conductive separator material 84 encapsulating either one or both of the first electrode 80 and the second electrode 82. These three components are generally placed together to form the electrode assembly 44. As is known in the art, the first electrode 80 and second electrode 82 will form an anode and a cathode of the battery 38.

The details regarding construction of the electrode assembly 44, with respect to materials and techniques may correspond to those disclosed for example in U.S. Pat. No. 7,544,220 entitled "Welding Methods and Apparatus for Batteries" issued to Zhao et al. and incorporated herein by reference in its entirety. The electrode assembly 44 can be a wound or coiled structure similar to those disclosed for example in U.S. Pat. No. 5,486,215 (Kelm et al.). The electrode assembly 44 can also be part of batteries in which the electrode types include spirally-wound, stacked plate, or serpentine, as disclosed, for example, in U.S. Pat. Nos. 5,312,458 and 5,250,373. Alternatively, in certain embodiments, the battery 38 can include single cathode electrodes as described, for example, in U.S. Pat. No. 5,716,729. The composition of the electrode assembly 44 can include any known battery chemistry, including a wound core of lithium/silver vanadium oxide (Li/SVO) battery as discussed for example in U.S. Pat. No. 5,458,997.

Figure 6:
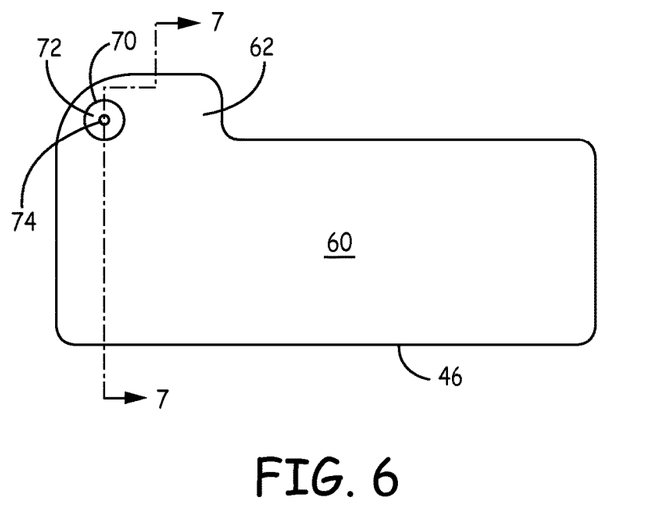
FIG. 6 shows a top profile of a battery cover with a feedthrough assembly.
Figure 7:
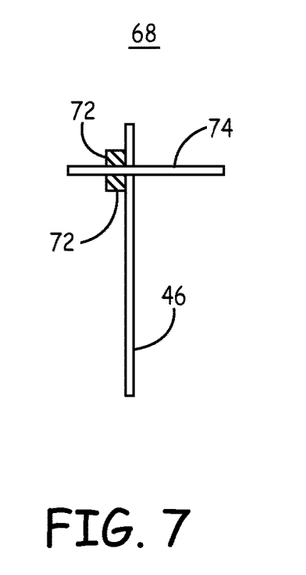
FIG. 7 shows a side profile of a battery cover with a feedthrough assembly.

With reference to FIGS. 6 and 7, a top and side profile of a battery cover 46 with a feedthrough assembly is shown. Battery cover 46 is comprised of an electrode assembly region 60, a headspace region 62, and a feedthrough assembly 68. Battery cover 46 is designed to fit overtop the opening of a perimeter of the open end of battery case 42. As previously mentioned, the battery cover 46 rests on the lip of the open end such that it is substantially flush with the top of the opening of the battery case 42. As used in this disclosure, substantially flush may refer to the overlap between the battery cover and the battery case having a proportion of between 60% to 100%, and preferably about 98 to 100%. This provides for substantial ease of manufacturing when battery cover 46 is laser welded to battery case 42.

As shown in the side profile view of FIG. 7, taken along lines 7-7, the feedthrough assembly 68 contains a ferrule (not shown), an insulating member 72, and a feedthrough pin 74. In certain embodiments, the feedthrough pin 74 is formed of aluminum containing titanium alloy, as is described in U.S. Pat. No. 6,855,456, the disclosure of which is incorporated herein by reference. Accordingly, when such is used as the feedthrough pin 74, the likelihood of the pin 74 corroding is reduced, and thus, the likelihood of the corrosive materials escaping from the battery housing is reduced as well. However, it should be appreciated that any conductive material could be utilized for the feedthrough pin 74 without departing from the spirit of the invention.

The feedthrough pin 74 is generally conductively insulated from the battery cover 46 by the insulating member 72. The insulating member 72, which is generally comprised of CABAL-12 (calcium-boron-aluminate), TA-23 glass or other glasses, provides electrical isolation of the feedthrough pin 74 from the battery cover 46. The material of feedthrough pin 74 is in part selected for its ability to join with the insulating member 72, which results in a hermetic seal. As mentioned above, the pin material is also selected to be corrosion resistant. CABAL-12 is also generally corrosion resistant and a good insulator. Therefore, CABAL-12 provides good insulation between the feedthrough pin 74 and the battery cover 46 and is resistant to the corrosive effects of the electrolyte. However, other materials besides glass can be utilized, such as ceramic materials, without departing from the spirit of the invention.

Coupling between the electrodes and the externally accessible battery terminals such as feedthrough pin 74 and cover 46, e.g., via electrical connection to the tabs extending from the electrodes, can be difficult for several reasons. One reason involves differences in the physical properties of the pins and the tabs. This dissimilarity in material properties can lead to brittle joints or other unacceptable performance-related problems. To address such problems, current coupling methods have often involved use of a coupling member or manipulating the tab and/or the feedthrough pin for initial retention purposes before using a coupling process to achieve a secure joint between the tab and the pin. Unfortunately, these methods have been found to be highly sensitive to manufacturing variability (e.g., weld damage, coil damage, tab damage and missed welds), resulting in unstable manufacturing yield. The present invention is directed to overcoming, or at least reducing the effects of, one or more of the problems set forth above.

Figure 8:
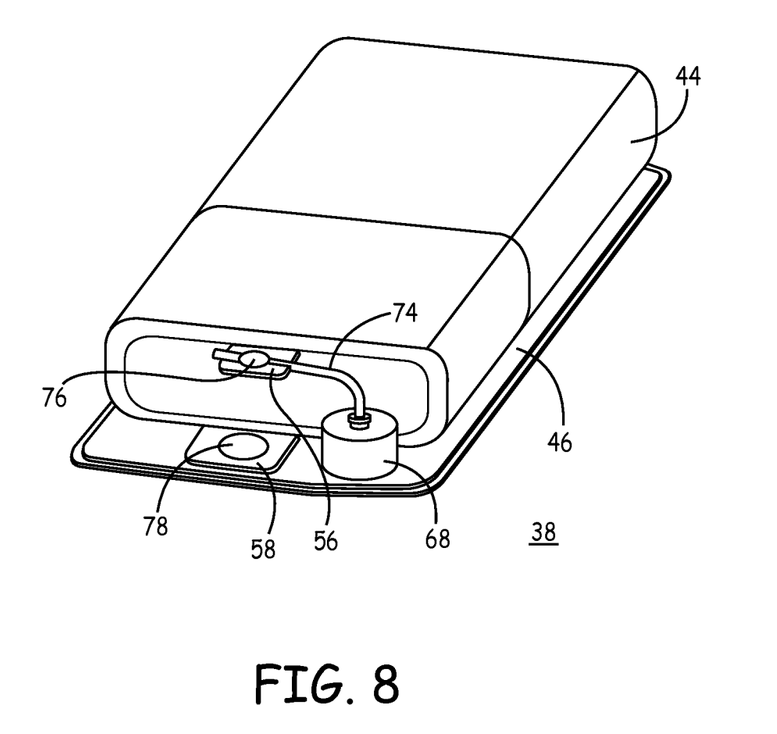
FIG. 8 illustrates an exploded view of the battery shown in FIG. 3.

FIG. 8 illustrates an exploded view of the battery 38 shown in FIG. 3. The battery 38 is shown with the electrode assembly 44 that includes first electrode tab 56 and second electrode tab 58. While the electrode assembly 44 is described as having first and second electrode tabs 56 and 58 respectively, it is fully contemplated each electrode could have more than one tab without departing from the spirit of the invention. One such electrode configuration involves each of the electrodes being subdivided over one or more electrode plates connected together and each electrode plate includes at least one tab protruding therefrom. The tabs of each electrode are coupled together to provide electrical continuity throughout the respective electrodes.

As will be described in more detail, one of the battery electrodes is operatively coupled to a first feedthrough mechanism (e.g., a feedthrough pin 74), while the other electrode is electrically coupled to the case 42 (e.g., via a direct connection to the cover 46). Overall, these couplings are facilitated through the use of the electrode tabs. Thereafter, when the battery is subsequently used, current is able to flow from the electrode plates through the tabs to the corresponding battery electrical contact (e.g., feedthrough pin 74, battery case 42).

As mentioned above, the coupling of the tabs to the feedthrough pin 74 and the battery case 42 to provide an effective joint can be challenging, particularly if the feedthrough pin 74 and tabs are made of different materials. However, it is often a necessity to have the pin 74 and the tabs be made of different materials to ensure the battery remains hermetic.

The coupling techniques of the present disclosure facilitate miniaturization of the IMD 10. In particular, the techniques enable construction of a battery with a tight form factor that enables a reduction in the overall volume of the battery of IMD 10. As described in more detail in the '220 patent, the coupling techniques of conventional batteries allow for flexibility in determining weld position and weld size. In the construction of such exemplary batteries, the '220 patent describes positioning the tabs in a spaced apart orientation such that the tabs are generally parallel in relation to a major planar surface of the cover. This provides the benefit of flexibility of joining each of the tabs independently. Moreover, the requirement to position the tabs at laterally spaced apart locations, as shown generally in the '220 patent, allows for large tolerances with respect to positioning of the tab and feedthrough pin and hence affords increased manufacturability. Moreover, due to the dissimilar materials and the mismatched thicknesses of the tabs and feedthrough pin, the coupling techniques of the conventional batteries such as the '220 patent enable fabricating robust weld joints.

However, the inventors discovered that these desirable properties in the conventional coupling techniques such as those in the '220 patent pose challenges when the overall dimensions of the battery 38 are reduced.

Aided by the disclosure of the '220 patent, those skilled in the art can appreciate that due to the nature of the coiling process of the electrode assembly, once unloaded coils will shrink in width and expand in thickness. This action is reversed when the coils are inserted and compressed inside the battery case. Therefore, the inventors of the present disclosure have found that a very accurate coil alignment relative to the header has to be maintained during formation of the cathode and anode weld joints with the aforementioned reduction in the overall dimensions of the battery components.

But even with adjustments to the coil alignment, the inventors of the present disclosure have found that as the dimensions of the overall battery are reduced, the conventional coupling techniques result in warped tabs and create buckling of the anode during the coupling between the cover and the electrode assembly.

The overall reduction in the volume of the battery means that a reduction occurs in the space that is required for the conventional coupling techniques of battery electrode assemblies. At the very least, the tabs of such conventional batteries cannot overlap each other as there must be enough clearance between the coupling locations.

In accordance with embodiments of the present disclosure, techniques have been developed that permit simultaneous coupling of the tab 56 to the feedthrough pin 74 and tab 58 to the battery cover 46. The coupling techniques eliminate the need to manipulate the feedthrough pin or to utilize coupling components for forming the weld joints. The techniques enable the fabrication of a robust weld for a miniaturized battery.

Figure 9:
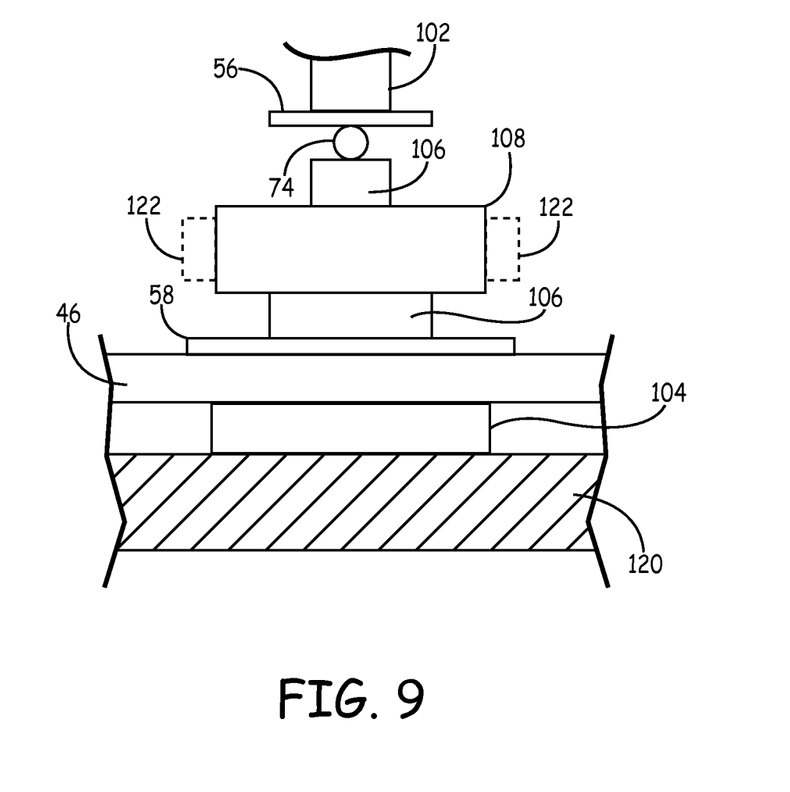
FIG. 9 illustrates a schematic diagram showing an embodiment of a coupling technique utilized for fabrication of a battery for the IMD.

FIG. 9 illustrates a schematic diagram showing an embodiment of a coupling technique utilized for fabrication of battery 38 for the IMD 10. As depicted, the feedthrough pin 74 is adjacent to tab 56 and the battery cover 46 is adjacent to the tab 58. Unlike the conventional batteries, the orientation of these components is such that a portion of all four components, i.e., feedthrough pin 74, tab 56, tab 58 and the battery cover 46 will be oriented in an overlapping relationship such that the portions are positioned along a common plane along lines Y-Y that is perpendicular to the plane defined by the major surface of the battery case 42 (shown in phantom lines).

In the illustrative embodiment, a coupling technique is utilized to simultaneously couple the tab 56 to the feedthrough pin 74 and tab 58 to the battery cover 46. As is shown in FIG. 8, the feedthrough pin 74 includes a first connection portion 76 and the anode tab includes a second connection portion 78 that are spaced apart, but overlap each other. As used in this disclosure, overlapped means that at least portions of the components, such as the tab 56, feedthrough pin 74, tab 58 and the battery cover 46, are positioned along a plane with no lateral spacing. Returning to FIG. 9, both the first connection portion 76 and the second connection portion 78 are oriented along the common plane illustrated by lines Y-Y that is perpendicular to a plane defined by the major surface of the bottom end of the battery case 42. Thus, a cathode weld joint is formed at the intersection of the tab 56 to the feedthrough pin 74 and an anode weld joint is formed at the intersection of the tab 58 to the battery cover 46. Based on this configuration, the cathode weld joint and anode weld joint can be formed simultaneously through any known welding operation. While not shown, it should be appreciated that in alternative embodiments, the cathode weld joint may be formed at the intersection of the tab 56 to the battery cover 46 and an anode weld joint is formed at the intersection of the tab 58 to the feedthrough pin 74.

Figure 10:
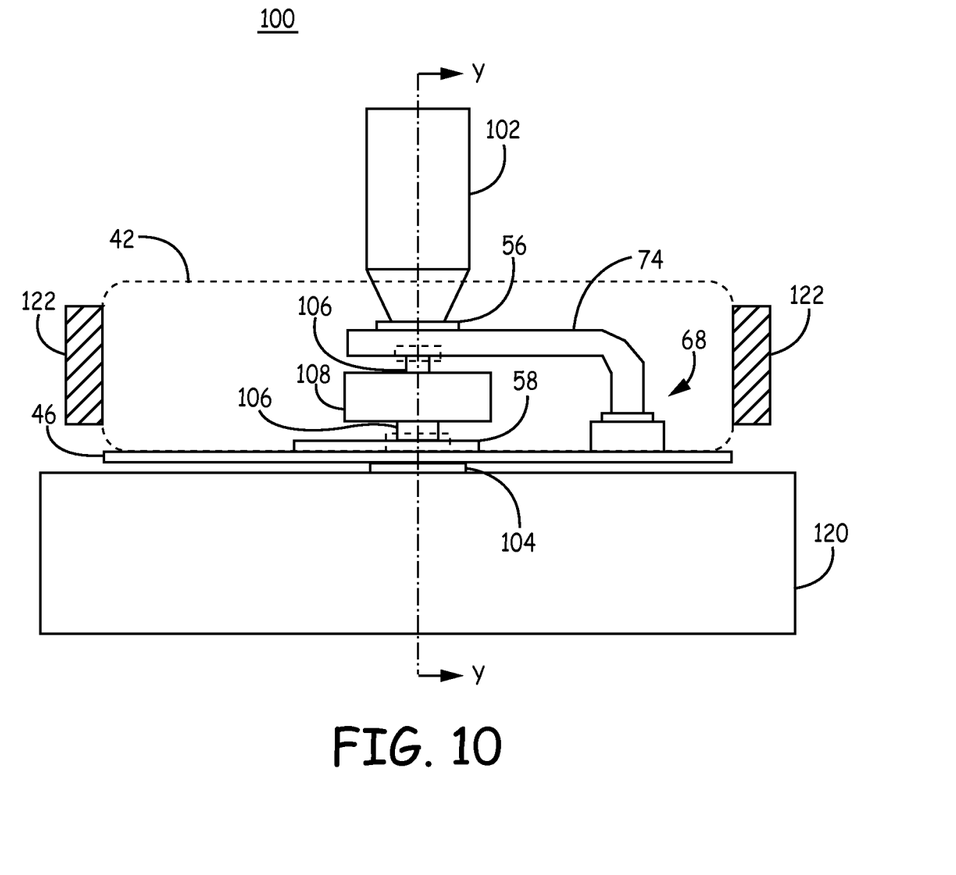
FIG. 10 is a schematic view of the coupling tool of FIG. 9 that is utilized in one embodiment for fabrication of a battery for an IMD.

In the illustrative embodiment of FIG. 9, a coupling technique discussed in more detail in FIGS. 9 and 10 is utilized to form the weld joints between the cathode tab 56 and the feedthrough pin 74, and the anode tab 58 and the cover 46. Briefly, the coupling technique utilizes resistance spot welding to form the mechanical connections that define the weld joints. However, aided with the benefit of this disclosure, it will be apparent to those skilled in the art that any suitable opposed welding process can be modified for the coupling process.

A coupling tool 100 having a set of electrodes 102, 104, and 106 is utilized in this embodiment for resistance spot welding. This process enables each of the electrodes 102, 104, and 106 to be dimensioned so as to provide adequate coverage over the weld location. Thus, the electrodes 102, 104, and 106 may be formed with dissimilar shapes and sizes as is desired to accommodate the surfaces of the cathode tab 56, the feedthrough pin 74, the anode tab 58, and the cover 46. Electrode 106 may be coupled to a compressive member 108.

The overall width of the electrode 106 including the compressive member 108 can be sized to approximately match the spacing between the feedthrough pin 74 and the cathode tab 58. The dimension of the electrode 106 including the compressive member 108 ensures that the desired spacing is maintained, while also providing a compressive force to hold the battery components together until a robust weld joint is formed.

With the above described orientation, the weld joint is formed by current that flows in series from the top electrode 102 through the cathode tab 56, the feedthrough pin 74, the middle electrode 106, the anode tab 58, the cover 46 and the bottom electrode 104. As such, both sets of welds can be produced simultaneously with this coupling technique.

In an alternate embodiment, the coupling techniques may utilize independent power supplies for formation of the weld joint between the cathode tab 56 and feedthrough pin 74 as well as the weld joint between the anode tab 58 and the cover 46. The electrodes 102, 104, and 106 may be coupled to a power source such that a first current supply flows through electrodes 102 to 106 and a second current supply that is different from the first current supply flows through electrodes 106 to 104. With this configuration, different levels of current can be delivered to form each of the cathode and anode weld joints. As stated above, the battery components may suitably be formed having dissimilar materials. As such, providing independent current supplies will enable the delivery of appropriate current supplies that are suitable for each set of materials.

The connection between the anode tab 58 and the cover 46 provides an electrical coupling for the power supply during operation of the battery 38. Additionally, the connection of the tab 58 to the cover 46 also serves to mechanically couple the electrode assembly 44 to the cover 46.

In accordance with some embodiments, the coupling tool 100 may include a securing mechanism 122 that is configured to retain the electrode assembly in a predefined configuration. The securing mechanism 122 may be embodied as a support frame to hold one or more of the components to be welded in a stationary position. For example, the securing mechanism 122 may be defined such that the electrode assembly is formed in a shape generally corresponding to that of the assembled electrode assembly once it is inserted in the case 42. The securing mechanism 122 may include an enclosed body having a hollow region generally corresponding to the receptacle defined by the case 42. In other embodiments, the securing mechanism 122 may include at least two rails that are spaced apart, to provide a width that generally corresponds to the width of the case and a third rail that is spaced apart from the bottom electrode 104.

The coupling tool 100 may include a platform 120 onto which the bottom electrode 104 may be positioned. The platform 120 in conjunction with the bottom electrode 104 will inhibit movement of the cover 46 during a welding cycle. In alternative embodiments, the bottom electrode 104 may be integrated onto the platform 120.

The securing mechanism 122 will hold the electrode assembly 44 and is moveable relative to the platform 120 so that the electrode assembly 44 can be positioned over the cover 46 to enable the tabs 56, 58 to be aligned as discussed above. The securing mechanism 122 may compress the electrode assembly to a pre-determined thickness that substantially corresponds to the dimensions of the interior of the battery case 42. As used in this disclosure, substantially may refer to the pre-determined thickness having a proportion of between 60% to 100%, and preferably about 90 to 99% of the internal volume of the battery case 42. In doing so, the securing mechanism 122 ensures proper alignment of the electrode assembly 44 with the cover 46 in both lateral and transverse directions, while also compressing the electrode assembly 44 to the pre-determined dimensions during the welding process. The securing mechanism 122 also provides for the alignment of the tabs 56, 58 in an overlapping orientation for the simultaneous coupling of the tabs to the feedthrough pin 74 and cover 46.

FIG. 10 is a schematic view of the coupling tool 100 of FIG. 9 that is utilized in one embodiment for fabrication of a battery for an IMD. The coupling tool 100 enables simultaneous welding of a first set of components and a second set of components. For example, the first set of components may include the feedthrough pin 74 and tab 56 and the second set of components may include the tab 58 and the cover 46. As is known in the art, resistance spot welding may be utilized to create a bond between a pair of components.

By way of general explanation and described with reference to FIG. 10, resistance spot welding may be carried out via coupling tool 100 (partially shown) that may include a power supply (not shown) for electrical current supply and electrodes configured for clamping together each of the sets of components, as set forth in more detail below.

Conventional spot welding tools utilize a pair of axially aligned and opposing electrodes that press upon opposite sides of the component pair to be bonded for formation of individual weld joints. Therefore, the need for the dual opposed pressing action from the axially aligned electrodes means that only one weld joint can be created for any given opposing electrode pair.

The coupling tool 100 is configured having a top electrode 102, a bottom electrode 104 and an opposed electrode 106. The coupling tool 100 is utilized in a bonding operation that forms two discrete weld joints simultaneously. In the illustrative embodiment, the weld joints are formed on two sets of components. The coupling tool 100 is configured such that the two sets of components are oriented in an overlapping relationship along a common lateral axis. As such, the welding current flows from the top electrode 102 through the opposed electrode 106 to the bottom electrode 104. Thus, the coupling tool 100 is configured to create a first bond between the first set of components, such as the feedthrough pin 74 and tab 56, and a second bond between the second set of components such as the tab 58 and the cover 46.

As is described in more detail with reference to the electrodes in the embodiment of FIG. 11, the electrodes 102-106 may be independently addressable. That is, the power supply includes independent current paths that are defined for each set of the electrodes 102, 106 and 106, 104. In this configuration, the power supply may suitably generate different current amounts for each independent current path. This embodiment may be of particular application for coupling components having dissimilar materials.

The shape and size of the tips of the electrodes 102, 104, 106 will control the distribution of heat at the location of the weld joint. Moreover, these dimensions will control the geometry of the weld joint. As such, the tips of each of the electrodes 102-106 will be selected having a predetermined shape. Examples of the predetermined shapes for the tips include domed, conical, or flat. Therefore, a given tip shape will be selected as a function of the material of the components to be coupled and the desired weld joint geometry. Preferably, the electrodes 102-106 may be formed with a contact surface area in the range of 0.03 inches to 0.08 inches.

In accordance with embodiments of this disclosure, a compressive force is suitably applied between the electrodes 102, 106 and electrodes 106, 104 to place the components under compression. Electrode 106 may include compressive member 108 to place the components between electrode 102 and electrode 106 under compression and the components between electrode 106 and electrode 104 under compression. The compression force between any two electrodes may be selected to generate direct physical contact between any two components to be bound. For example, a force in the range of 5 to 12 lbs may be applied between any two electrodes.

In an illustrative welding sequence, the coupling tool 100 is utilized to create a weld joint by application of current through the electrodes 102-106 coupled with a compressive force that is generated between the top electrode 102 and the opposed electrode 106, as well as the compressive force that is generated between the opposed electrode 106 and the bottom electrode 104. Without intending to be bound by theory, the current flowing across the electrodes generates heat at the intersection of the component surfaces and the electrodes 102-106. Coupled with the application of mechanical forces holding the components in place, the heat will cause the melting of the components with a subsequent re-solidification in the absence of current flow.

It is contemplated that the components in the first set of components may have dissimilar materials whereas the components in the second set of components may also have dissimilar materials, both of which are different from the materials of the first set of components.

Figure 11:
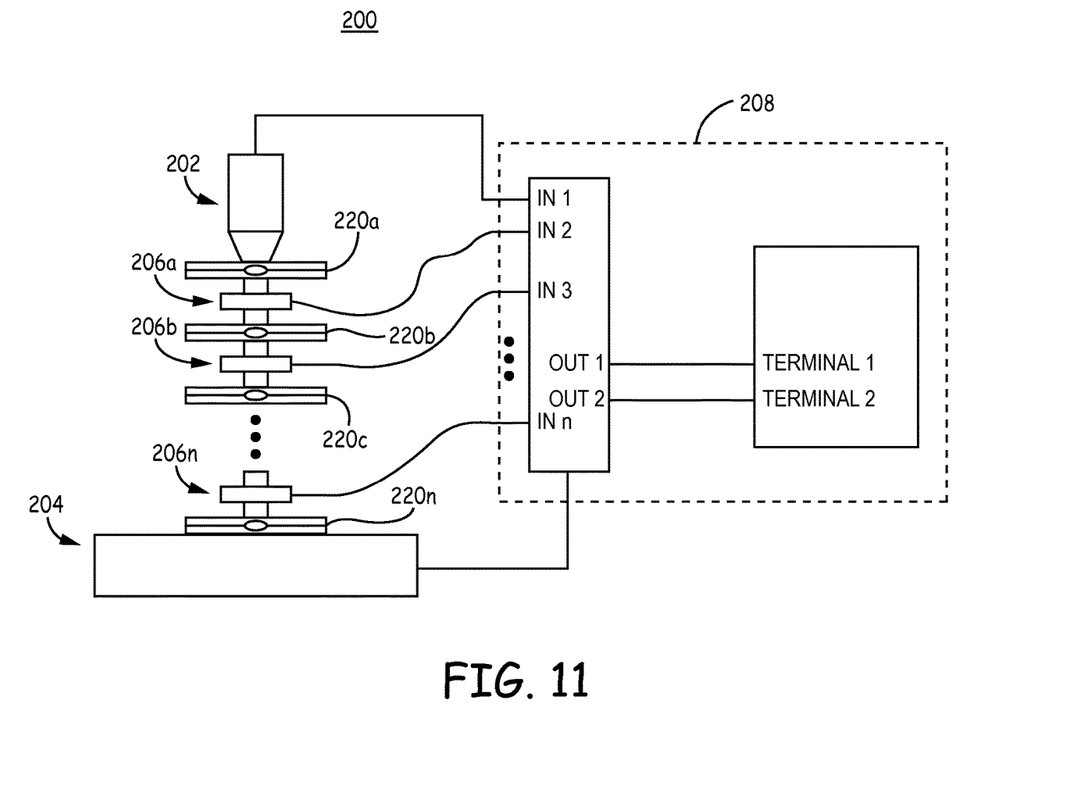
FIG. 11 depicts an alternate embodiment of a coupling tool for performing a coupling operation.

FIG. 11 depicts an alternate embodiment of a coupling tool 200 for performing a coupling operation. The coupling tool 200 may suitably be used for forming a plurality of weld joints 220 in a device such as the battery 38. For example, coupling tool 200 may be suitable for coupling a battery having more than two overlapping tabs to externally accessible terminals.

Coupling tool 200 includes a top electrode 202, a bottom electrode 204, and a plurality of opposed electrodes 206a, 206b, and 206n. Although only three opposed electrodes 206a, 206b and 206n are shown, it is contemplated that the tool 200 may include any number of electrodes. Similar to the electrodes of the coupling tool 200, the shape and size of each of electrodes 202-206 can also be varied to control the heat balance to each weld joint.

A weld power supply 208 is provided for generating the weld current that is utilized during the welding operation. The weld power supply 208 may include multiple supply outlets for electrical connections to each of the electrodes. This enables the formation of independent current paths for each of the weld joints or for groupings of weld joints.

It will be appreciated the present invention can take many forms and embodiments. The true essence and spirit of this invention are defined in the appended claims, and it is not intended the embodiment of the invention presented herein should limit the scope thereof.

The foregoing discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein.

What is claimed is:

1. A battery, comprising:
    a case having a top end, a bottom end, and a plurality of sides extending from the bottom to define a cavity;
    a cover configured to enclose the top end of the case and having a feedthrough pin;
    an electrode assembly disposed within the cavity, the electrode assembly having an anode, a cathode and an electrolyte; and
    an anode tab coupled to the anode and a cathode tab coupled to the cathode, wherein the anode tab is electrically coupled to the cover and the cathode tab is electrically coupled to the feedthrough pin;
    an anode weld joint formed at an intersection of the anode tab to the cover such that the anode tab is welded to the cover; and
    a cathode weld joint formed at an intersection of the cathode tab to the feedthrough pin such that the cathode tab is welded to the feedthrough pin;
    wherein at least a predefined width of the anode tab is configured to overlap a segment of the cathode tab along a plane that is perpendicular to a plane oriented along the bottom end and perpendicular to the predefined width of the anode tab, and further wherein the anode weld joint and the cathode weld joint are located along the plane.

2. The battery of claim 1, wherein the anode weld joint electrically couples the anode tab to the cover and the cathode weld joint electrically couples the cathode tab to the feedthrough pin.

3. The battery of claim 2, wherein the anode tab and the cathode tab are oriented such that the anode weld joint and the cathode weld joint are operably formed simultaneously via a resistance spot welding coupling.

4. The battery of claim 2, wherein the feedthrough pin includes a first connection portion that is oriented along a first plane with respect to a second connection portion of the anode tab so that the first connection portion and the second connection portion are aligned to overlap along a plane that is common with a plane defined by the cathode weld joint and the anode weld joint.

5. The battery of claim 1, further comprising an electrical insulator disposed between the case and the electrode assembly.

6. The battery of claim 5, wherein the electrical insulator is configured having a tab separator that includes a predetermined spacing such that the tab separator is positioned between the anode tab and the cathode tab.

7. The battery of claim 1, wherein the electrode assembly is configured in a coiled structure.

8. The battery of claim 1, wherein the electrode assembly is a stacked plate assembly of the one or more electrodes.

9. The battery of claim 1, wherein the feedthrough pin and the cathode tab are formed from dissimilar materials.

* * * * *